United States Patent
Balasubramanian et al.

(10) Patent No.: US 11,325,879 B2
(45) Date of Patent: May 10, 2022

(54) METHODS OF MAKING PURIFIED FATTY ACID COMPOSITIONS

(71) Applicant: The Procter & Gamble Company, Cincinnati, OH (US)

(72) Inventors: Rajesh Kumar Balasubramanian, Singapore (SG); Mohammad Rasoul Madadi, Singapore (SG); Jovina Zhi Qi Tan, Singapore (SG)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 17/062,730

(22) Filed: Oct. 5, 2020

(65) Prior Publication Data
US 2021/0114965 A1  Apr. 22, 2021

(30) Foreign Application Priority Data
Oct. 17, 2019 (EP) .................................... 19203722

(51) Int. Cl.
*C07C 51/47* (2006.01)
*C11B 3/10* (2006.01)

(52) U.S. Cl.
CPC .............. *C07C 51/47* (2013.01); *C11B 3/10* (2013.01)

(58) Field of Classification Search
CPC ......... C07C 51/47; C07C 53/126; C11B 3/10; C11C 1/005
See application file for complete search history.

(56) References Cited

U.S. PATENT DOCUMENTS

| | | | | |
|---|---|---|---|---|
| 1,740,012 A * | 12/1929 | Godal | ...................... | C11C 1/08 554/96 |
| 2,475,420 A | 7/1949 | Brown | | |
| 2,714,603 A * | 8/1955 | Goebel | ...................... | C11C 1/04 554/155 |
| 4,781,864 A | 11/1988 | Pryor | | |
| 5,814,209 A | 9/1998 | Haehn | | |
| 6,027,755 A * | 2/2000 | Henderson | ............... | B01J 20/12 426/253 |
| 7,169,946 B1 * | 1/2007 | Thode | ...................... | C11B 3/10 554/191 |
| 7,459,574 B2 * | 12/2008 | Richard-Elsner | ....... | C11B 3/001 554/175 |
| 7,579,299 B2 * | 8/2009 | Flessner | .................. | B01J 20/10 423/327.1 |
| 2005/0043555 A1 * | 2/2005 | Garro | ..................... | C11C 1/007 554/126 |

FOREIGN PATENT DOCUMENTS

GB  1278379 A  6/1972

OTHER PUBLICATIONS

International Search Report and Written Opinion; Application Ser. No. PCT/US2020/070666; dated Nov. 23, 2020, 10 pages.
Christidis, George E., et al.; Decolorization of Vegetable Oils: A Study of the Mechanism of Adsorption of β-Carotene By an Acid-Activated Bentonite From Cyprus; Clays and Clay Minerals; vol. 51, No. 3, pp. 327-333; 2003.
Extended European Search Report; Application No. 19203722.4-1106; dated Mar. 23, 2020; 7 pages.
Joy, Nde-Aga Binwie, et al.; Adsorption of Palm Oil Carotene and Free Fatty Acids onto Acid Activated Cameroonian Clays; Journal of Applied Sciences; ISSN 1812-5654; 7(17), pp. 2462-2467; 2007.

\* cited by examiner

*Primary Examiner* — Yate' K Cutliff
(74) *Attorney, Agent, or Firm* — George H. Leal

(57) ABSTRACT

Certain bleached earths improve methods of fatty acid purification.

20 Claims, No Drawings

METHODS OF MAKING PURIFIED FATTY ACID COMPOSITIONS

FIELD OF THE INVENTION

The present invention is directed to purifying fatty acid compositions, specifically methods of making purified fatty acid compositions having improved color values and/or color stability over time.

BACKGROUND OF THE INVENTION

Fatty acids are produced by hydrolyzing natural fats, that is, glyceryl esters of fatty acids, into a mixture of fatty acids and glycerin, and separating the fatty acids from glycerin. While natural fats consist predominantly of glyceryl esters, natural fats also contain impurities or substances which, when exposed to heat and/or atmospheric conditions, become darkened in color. Also, commercial fatty acids generally are derived from more impure, inedible oils and fats which in and of themselves are of dark color. Thus, a batch of fatty acids produced commercially by hydrolysis is usually brown in color, or darker, depending upon the quality of the feed stock put into the hydrolyzer. These crude/raw fatty acids sometimes are bleached by addition of bleaching earth capable of adsorbing at least some of the dark colored components. Bleaching of fatty acids is accomplished by mixing with the fatty acids an amount of bleaching earth required to give the desired color, usually 1-3 percent by weight, and agitating from 15-30 minutes at a temperature of approximately 70 degrees Celsius. Thereafter, the bleaching agent is removed by filtration.

There is a continuing need to select bleaching agents in methods of making purified fatty acid compositions specifically as it relates to the reduction of color.

SUMMARY OF THE INVENTION

The present invention is based, at least in part, upon the surprising observation that acid activated bleaching earths characterized herein, provides purified fatty acid compositions having desirably reduced color values. That is, the use of these certain bleaching earths can reduce the resulting Lovibond color values thereby indicating a higher degree of purification in purified fatty acid compositions. Accordingly, an aspect of the invention provides for a method of making a purified fatty acid composition comprising the step of combining a raw fatty acid composition with a bleaching earth having a pH less than 3.9. The pH of the bleaching earth is assessed by a 10 percent by weight suspension of the bleaching earth and distilled water filtered through polytetrafluoroethylene filter paper, and at 25 degrees Celsius. Optional additional steps may include mixing the combined raw fatty acid composition and bleaching earth and/or filtering the (mixed) combined raw fatty acid composition and bleaching earth to remove the bleaching earth.

An advantage of the present invention is stabilization of the purified fatty acid composition against color deterioration during storage or during use.

An advantage of the present invention is minimizing the use of the subject bleaching earth.

An advantage of the present invention is avoiding the need for nitrogen blanketing in the handling, storage, and/or transportation of the purified fatty acid composition.

An advantage of the present invention is avoiding, or at least minimizing, the need for expensive capital equipment and/or energy demands (e.g., hydrogenation requires pressured vessels, higher temperatures, catalyst, and/or re-distillation)).

DETAILED DESCRIPTION OF THE INVENTION

It is to be understood that the scope of the claims is not limited to the specific devices, apparatuses, methods, conditions or parameters described and/or shown herein, and that the terminology used herein is for the purpose of describing particular embodiments by way of example only and is not intended to be limiting to the claimed invention. Also, as used in the specification including the appended claims, the singular forms "a", "an", and "the" include the plural.

As used herein, any of the terms "comprising", "having", "containing", and "including" means that other steps, ingredients, elements, etc. which do not adversely affect the end result can be added. Each of these terms encompasses the terms "consisting of" and "consisting essentially of". Unless otherwise specifically stated, the elements and/or equipment herein are believed to be widely available from multiple suppliers and sources around the world.

An aspect of the invention provides for a method of making a purified fatty acid composition comprising the steps of combining a raw fatty acid composition with a bleaching earth having a pH less than 3.9. The pH of the bleaching earth is assessed at 25 degrees Celsius from a water extract of the bleaching earth, wherein the water extract is a 10 percent by weight suspension of the bleaching earth and distilled water filtered through polytetrafluoroethylene filter paper, and at 25 degrees Celsius. Preferably the assessed pH of the water extract of bleaching earth is less than 3.7, preferably less than 3.5, more preferably less than 3.3. Alternatively, the pH is from 2.5 to 3.5, or alternatively about 3.1. Without wishing to be bound by theory, surface charges and/or acidic sites help to attract charged impurities. Optional additional steps may include mixing the combined ray fatty acid composition and bleaching earth and/or filtering the (mixed) combined raw fatty acid composition and bleaching earth to remove the bleaching earth.

In the oil, fat, and fatty acid industries color values are usually determined by the Lovibond method. Generally, the lower the Lovibond color, the purer the purified fatty acid composition. The method of assessing Lovibond Red value and Lovibond Yellow value is by way of the AOCS (American Oil Chemists' Society) Official Method Cc13b-45, reapproved 2017 (AOCS, Urbana, Ill., USA). It is used to assess the color of fats and oils using color glasses calibrated in accordance with the AOCS-Tintometer Color Scale.

Acid activated bleaching earths are compared to comparative bleaching earths for its effectiveness in Lovibond color reduction in treated fatty acids. A 60 gram ran fatty acid composition (CAS-No 68937-75-7) comprising decanoic acid and octanoic acid is combined with inventive bleaching earths examples 1 and 2, as well as comparative bleaching earths examples A and B. Examples 1 and 2 are Cela Celar-160™ and Fitrol-160 ™ both from EP Minerals, respectively. Examples A and B are Tonsil 1204™ and Tonsil. 1206™ both from Clariant. The combined raw fatty acid composition and bleaching earth is mixed at 350 rotations per minute at 25 degrees Celsius for 6 hours. The mixed combined raw fatty acid composition and bleaching earth is filtered using a 0.45 micron syringe filter. The pH of the bleaching earth is assessed by a 10 percent by weight suspension of the bleaching earth and distilled water filtered through polytetrafluoroethylene filter paper, and at 25 degrees Celsius. The Lovibond Red and Yellow values of the treated fatty acid composition are assessed by way of the AOCS Official Method Cc13b-45, reapproved 2017. As indicated in Table 1 below, examples 1 and 2 are more effective than comparative examples A and B in reducing Lovibond Red and Yellow values in treated fatty acids.

TABLE 1 pH of inventive and comparative bleaching earths and resulting Lovibond values in treated fatty acids.

| Bleaching Earth Example | pH of Water Extract Example | Weight % of Bleaching Earth | Purified Fatty Acid Color | |
|---|---|---|---|---|
| | | | Lovibond Red (R) | Lovibond Yellow (Y) |
| Control | — | 0 wt % | 0.6 | 2.6 |
| 1 | 3.1 | 0.5 wt % | 0.0 | 0.7 |
| 2 | 3.1 | 0.5 wt % | 0.0 | 0.7 |
| A | 3.9 | 4.0 wt % | 0.2 | 0.9 |
| B | 3.9 | 4.0 wt % | 0.2 | 0.9 |

Acid activated bleaching earth with higher residual acidity can reduce the Lovibond Red color to zero and Lovibond Yellow to around 0.6 at 0.5% of bleaching earth by weight of the combined fatty acid composition and bleaching earth. Even with eight times increase in the amount of the comparative bleaching earth, these comparative examples A and B could not reduce the Lovibond Red value below 0.2. Without wishing to be bound by theory, surface acidity may play a significant role in color removal performance of bleaching earths.

An aspect of the methods described herein provides for a bleaching earth comprising a mean particle size less than 43 microns, preferably less than 40 microns, more preferably less than 35 microns, alternatively from 22 microns to 30 microns, wherein the mean particle size is determined by way HORIBA laser scattering particle size distribution analyzer. Inventive examples 1 and 2 both have smaller mean particle sizes than comparative examples A and B. Inventive examples 1 and 2 contain more the particle fraction under 10 microns compared to comparative examples A and B.

TABLE 2

Laser Scattering Particle Size Distribution Analyzer LA-950 data for inventive and comparative bleaching earths.

| | Bleaching Earth Examples | | | |
|---|---|---|---|---|
| Parameter | 1 | 2 | A | B |
| Median Size | 13.1 | 20.3 | 33.3 | 41.4 |
| Mean Size | 22.3 | 30.4 | 42.8 | 53.8 |
| Std Dev | 25.4 | 29.8 | 36.0 | 45.7 |
| Geo. Mean Size | 14.2 | 20.0 | 29.0 | 36.7 |
| Geo. Std. Dev. | 2.5 | 2.6 | 2.7 | 2.7 |
| Mode Size | 10.8 | 14.2 | 48.0 | 55.0 |
| Wt % of particles under 10 microns | 38 wt % | 25 wt % | 13 wt % | 9 wt % |

An aspect of the methods described here provide for an average pore width off less than 7.7 nanometers, preferably less than 7 nm, more preferably less than 6.5 nm, yet even more preferably less than 6 nm, alternatively from 5 nm to 6 nm, or from 5.5 nm to 6 nm. Bleaching earth examples 1 and 2 have a pore width of 5.8 nm, while comparative examples A and B have a pore width of 7.8 nm and 7.7 nm, respectively.

An aspect of the methods described herein provide for a bleaching earth comprises at least 14 wt % of particles having a particles size of less than 10 microns. Preferably at least 15 wt %, more preferably at least 20 wt %, alternatively from 25 wt % to 38 wt %, of said particles having a size of less than 10 microns. The particle size is determined by way HORIBA laser scattering particle size distribution analyzer.

Color body impurities adsorption by the bleaching earth could be, at least in part, by chemisorption. Accordingly, atomic components of the bleaching earth may contribute to the color removal performance. An aspect of the methods provided here provides a bleaching earth comprising an atomic percentage distribution of Sulfur greater than 1.2% by weight of the bleaching earth, preferably greater 1.7%, more preferably greater than 2%, alternatively from 2.0% to 2.5%, as determined by X-ray photoelectron spectroscopy. X-ray photoelectron spectroscopy (XPS) is a surface-sensitive quantitative spectroscopic technique that measures the elemental composition at the part per thousand range, empirical formula, chemical state, and electronic state of the elements that exist within a material. Another aspect provides a bleaching earth comprising an atomic percentage distribution of Potassium less than 0.6% by weight of the bleaching earth, preferably less than 0.4%, more preferably less than 0.2%, alternatively about 0%, as determined by X-ray photoelectron spectroscopy. Another aspect provides a bleaching earth comprising an atomic percentage distribution of Iron less than 1.1% by weight of the bleaching earth, preferably less than 1%, more preferably less than 0.8%, alternatively from 0.3% to 0.9%, as determined by X-ray photoelectron spectroscopy. Table 3 provides atomic composition of inventive and comparative bleaching earths.

TABLE 3

Atomic composition of inventive and comparative bleaching earths.

| Bleaching Earth Examples | Atomic Composition (Weight Percentage) | | | | | | | | |
|---|---|---|---|---|---|---|---|---|---|
| | $C_{1S}$ | $O_{1S}$ | $Mg_{1S}$ | $Al_{2p}$ | $Si_{2p}$ | $S_{2s}$ | $K_{2p}$ | $Ca_{2s}$ | $Fe_{2p}$ |
| 1 | 1.1 | 69.1 | 1.0 | 4.3 | 19.5 | 2.2 | 0.0 | 2.1 | 0.7 |
| 2 | 1.5 | 67.4 | 1.0 | 4.5 | 21.5 | 2.2 | 0.0 | 1.2 | 0.6 |
| A | 1.6 | 68.4 | 1.5 | 3.9 | 20.4 | 1.2 | 0.8 | 0.9 | 1.4 |
| B | 1.6 | 66.8 | 1.9 | 4.2 | 21.5 | 1.0 | 0.6 | 1.4 | 1.1 |

Crystal structure of Bleaching Earth Examples 1 and 2 are compared to comparative Examples A and B. X-ray Powder Diffraction (XRD) data indicate that Examples 1 and 2 contain more crystalline materials than comparative Examples A and B. To this end, Examples 1 and 2 may contain montmorillonite, calcium anhydrite, and nontronite. In contrast, Examples A and B are mostly amorphous and may contain chlorite-vermiculite, albite, and merwinite. Without wishing to be bound by theory, crystal structure may play a role in color removal performance of bleaching earths.

An aspect of the invention provides a method of making a purified fatty acid composition, wherein the purified fatty acid composition, preferably filtered purified fatty acid composition, comprises a Lovibond Red value, per AOCS Official Method Cc 13b-45 2017, of less than 0.2, preferably from 0.1 to 0, more preferably about 0. Preferably the purified fatty acid, preferably filtered purified fatty acid composition, comprises a Lovibond Yellow value, per AOCS Official Method Cc 13b-45 2017, of less than 1, preferably less than 0.9, more from less than 0.9 to 0, yet even more preferably less than 0.6, yet still even more preferably from 0.5 to 0.

Preferably the combined raw fatty acid composition and bleach earth comprising at least 0.3% by weight of the bleaching earth, preferably at least 0.4 wt %, more preferably at least 0.3 wt % but not greater than 1 wt %.

Preferably the raw fatty acid composition comprises greater than 50 wt %, preferably from 60 wt % to 100 wt %, more preferably from 80 wt % to 100 wt %, yet more preferably from 90 wt % to 99.99 wt % of fatty acids. Preferably the raw fatty acid composition comprises: decanoic acid [CAS No. 334-48-5]; and octanoic acid [CAS No. 124-07-02]; preferably at least 35 wt % of said decanoic acid and at least 35 wt % said octanoic acid, by weight of the raw fatty acid composition.

Preferably the purified fatty acid composition comprises decanoic acid and octanoic acid. More preferably the purified fatty acid composition comprises at least 35 wt % of said decanoic acid and at least 35 wt % said octanoic acid, by weight of the raw fatty acid composition. Even more preferably the purified fatty acid composition comprises from 50 wt % to 65 wt % of said octanoic acid, from 35 wt % to 50 wt % of said decanoic acid, and from 0 wt % to 5 wt % of other ingredients.

In an example, the methods herein describe further comprise a preceding step of further comprising the preceding step of oil splitting crude palm kernel oil, crude coconut oil, or combination thereof to provide the raw fatty acid. In an example, the raw fatty acid composition having Lovibond Red (R) value greater than 0.5, even at or greater than 0.6; and/or a Lovibond Yellow (Y) value greater than 1.5, or greater than 2, or greater than 2.5, or even at or greater than 2.6. In one example, the raw fatty acid composition comprises octanoic acid and/or decanoic acids.

Preferably, the raw fatty acid composition and bleaching earth is combined and mixed from 5 minutes to 60 minutes, preferably from 10 minutes to 45 minutes, alternatively from 15 minutes to 35 minutes. Preferably the purified fatty acid composition is filtered to remove the bleaching earth.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical limitations were expressly written herein.

What is claimed is:

1. A method of making a purified fatty acid composition, the method comprising:
    combining a raw fatty acid composition with a bleaching earth, the bleaching earth having a pH less than 3.9, wherein the pH of the bleaching earth is assessed at 25 degrees Celsius from a water extract of the bleaching earth, wherein the water extract is a 10 percent by weight suspension of the bleaching earth and distilled water filtered through polytetrafluoroethylene filter paper.

2. The method of claim 1, wherein the pH of the water extract of the bleaching earth is less than 3.7.

3. The method of claim 1, further comprising:
    filtering a combination of the raw fatty acid composition and the bleaching earth to remove the bleaching earth to make the purified fatty acid composition.

4. The method of claim 1, wherein the purified fatty acid composition comprises Lovibond Red value, per AOCS Official Method Cc 13b-45 2017, of less than 0.2.

5. The method of claim 1, wherein the purified fatty acid composition comprises of Lovibond Yellow value, per AOCS Official Method Cc 13b-45 2017, of less than 1.

6. A method of making a purified fatty acid composition, the method comprising:
    (i) combining a raw fatty acid composition with a bleaching earth, the bleaching earth having a pH less than 3.3, wherein the pH of the bleaching earth is assessed at 25 degrees Celsius from a water extract of the bleaching earth, wherein the water extract is a 10 percent by weight suspension of the bleaching earth and distilled water filtered through polytetrafluoroethylene filter paper;
    (ii) mixing the combined raw fatty acid composition and bleaching earth; and
    (iii) filtering the mixed combined raw fatty acid composition and bleaching earth to remove the bleaching earth to make the purified fatty acid composition;
    wherein the purified fatty acid composition comprises: (i) a Lovibond Red value, per AOCS Official Method Cc 13b-45 2017, from 0.1 to 0; and (ii) a Lovibond Yellow value, per AOCS Official Method Cc 13b-45 2017, from 0.5 to 0.

7. The method of claim 1, wherein the bleaching earth comprises a mean particle size less than 43 microns, and wherein the mean particle size is determined by a laser scattering particle size distribution analyzer.

8. The method of claim 6, wherein the bleaching earth comprises a mean particle size less than 35 microns, and wherein the mean particle size is determined by a laser scattering particle size distribution analyzer.

9. The method of claim 1, wherein the bleaching earth comprises at least 14 wt % of particles having a particle size of less than 10 microns, and wherein the particle size is determined by a laser scattering particle size distribution analyzer.

10. The method of claim 8, wherein the bleaching earth comprises at least 20 wt %, of the particles having a size of less than 10 microns, and wherein the particle size is determined by a laser scattering particle size distribution analyzer.

11. The method of claim 1, wherein the bleaching earth comprises an atomic percentage distribution of Sulfur greater than 1.2% by weight of the bleaching earth, as determined by X-ray photoelectron spectroscopy.

12. The method of claim 10, wherein the bleaching earth comprises an atomic percentage distribution of Sulfur greater than 2% by weight of the bleaching earth, as determined by X-ray photoelectron spectroscopy.

13. The method of claim 1, wherein the bleaching earth comprises an atomic percentage distribution of Potassium less than 0.6% by weight of the bleaching earth, as determined by X-ray photoelectron spectroscopy.

14. The method of claim 1, wherein the bleaching earth comprises an atomic percentage distribution of Iron less than 1.1% by weight of the bleaching earth, as determined by X-ray photoelectron spectroscopy.

15. The method claim 1, wherein a combination of the raw fatty acid composition and the bleach earth comprises at least 3% but not greater than 1% by weight of the bleaching earth.

16. The method of claim 1, wherein the raw fatty acid composition comprises greater than 50 wt % of fatty acids.

17. The method of claim 1, wherein the raw fatty acid composition comprises at least decanoic acid and octanoic acid.

18. The method of claim 17, wherein the purified fatty acid composition comprises at least 35 wt % of the decanoic acid and at least 35 wt % of the octanoic acid, by weight of the raw fatty acid composition.

19. The method of any one of claim 1, further comprising: oil splitting crude palm kernel oil, crude coconut oil, or a combination thereof to provide the raw fatty acid composition.

20. The method of claim 10, further comprising: oil splitting crude palm kernel oil, crude coconut oil, or a combination thereof to provide the raw fatty acid composition; and wherein the purified fatty acid composition comprises from 50 wt % to 65 wt % of octanoic acid, from 35 wt % to 50 wt % of decanoic acid, and from 0 wt % to 5 wt % of other ingredients.

\* \* \* \* \*